(12) United States Patent
Robinson

(10) Patent No.: US 11,141,512 B2
(45) Date of Patent: Oct. 12, 2021

(54) SURGICAL DRAIN SYSTEM AND METHOD OF USE

(71) Applicant: SPECTRUM SPINE IP HOLDINGS, LLC, Atlanta, GA (US)

(72) Inventor: James C Robinson, Atlanta, GA (US)

(73) Assignee: Spectrum Spine IP Holdings, LLC, Atlanta, GA (US)

(*) Notice: Subject to any disclaimer, the term of this patent is extended or adjusted under 35 U.S.C. 154(b) by 917 days.

(21) Appl. No.: 15/545,269

(22) PCT Filed: Jan. 20, 2016

(86) PCT No.: PCT/US2016/014178
§ 371 (c)(1),
(2) Date: Jul. 20, 2017

(87) PCT Pub. No.: WO2016/118660
PCT Pub. Date: Jul. 28, 2016

(65) Prior Publication Data
US 2017/0368238 A1 Dec. 28, 2017

Related U.S. Application Data

(60) Provisional application No. 62/105,343, filed on Jan. 20, 2015.

(51) Int. Cl.
*A61M 1/00* (2006.01)
*A61M 27/00* (2006.01)
*A61M 39/24* (2006.01)

(52) U.S. Cl.
CPC ........ *A61M 1/0003* (2013.01); *A61M 1/0011* (2013.01); *A61M 1/78* (2021.05);
(Continued)

(58) Field of Classification Search
CPC .............. A61M 1/0003; A61M 1/0088; A61M 1/0049; A61M 27/00; A61M 1/0011;
(Continued)

(56) References Cited

U.S. PATENT DOCUMENTS 3,572,340 A 3/1971 Lloyd et al.
3,779,243 A 12/1973 Oakes et al.
(Continued)

OTHER PUBLICATIONS

International Search Report issued for corresponding International Application No. PCT/US2016/14178 dated Apr. 1, 2016.
(Continued)

*Primary Examiner* — Nicholas J Weiss
*Assistant Examiner* — Alessandro R Del Priore
(74) *Attorney, Agent, or Firm* — David L. King

(57) ABSTRACT

A surgical drain system for use during and following surgery is provided. A collection reservoir is placed in fluid communication with the body of a user through a collection port. A pump creates a vacuum pressure to urge fluid into the collection reservoir. Fluid exits the collection reservoir through a drain port. A drain mechanism allows air to come into the collection reservoir through an air intake aperture and collected fluid to leave the reservoir simultaneously. The drain system can be worn beneath clothes.

9 Claims, 2 Drawing Sheets

(52) U.S. Cl.
CPC .............. *A61M 1/90* (2021.05); *A61M 27/00* (2013.01); *A61M 1/63* (2021.05); *A61M 39/24* (2013.01); *A61M 2209/088* (2013.01)

(58) Field of Classification Search
CPC ................ A61M 1/0005; A61M 39/24; A61M 2209/088; A61M 1/0023; A61M 1/005; A61M 2209/084; A61M 2209/10; A61L 2/0088; A61L 2202/22; B08B 3/08; B08B 9/0936
See application file for complete search history.

(56) References Cited

U.S. PATENT DOCUMENTS

| | | | |
|---|---|---|---|
| 4,392,858 A * | 7/1983 | George | A61M 1/0011 604/126 |
| 4,457,755 A | 7/1984 | Wilson | |
| 4,569,674 A | 2/1986 | Phillips et al. | |
| 5,628,733 A | 5/1997 | Zinreich et al. | |
| 5,645,540 A * | 7/1997 | Henniges | A61M 1/0023 604/118 |
| 6,261,276 B1 | 7/2001 | Reitsma | |
| 6,652,495 B1 * | 11/2003 | Walker | A61L 2/0088 604/317 |
| 2011/0060300 A1 | 3/2011 | Weig et al. | |
| 2016/0067104 A1 * | 3/2016 | Sarangapani | A61M 1/0084 602/43 |

OTHER PUBLICATIONS

European Search Report issued for corresponding European Application No. 16740702.2 dated Jul. 9, 2018.

* cited by examiner

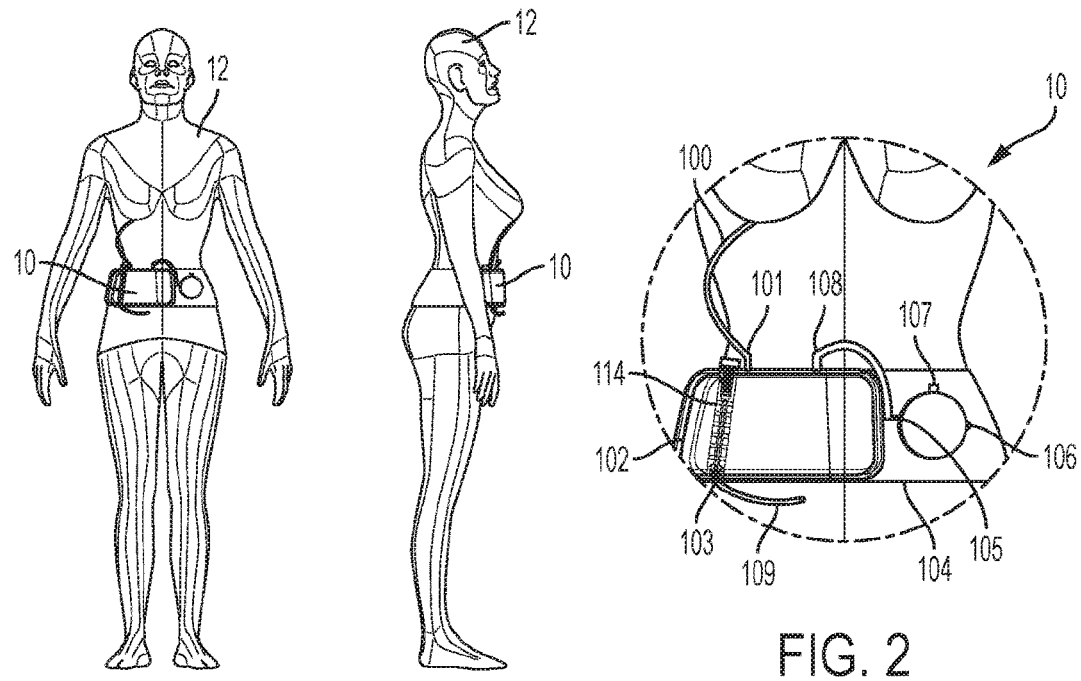
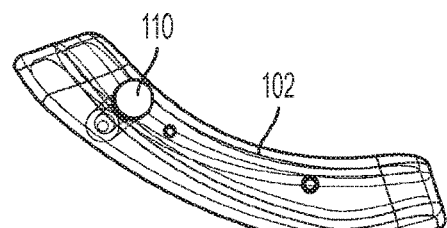
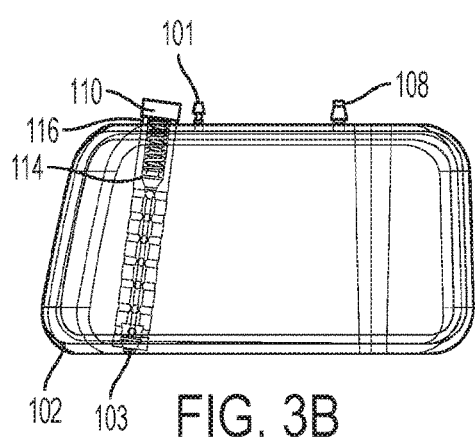
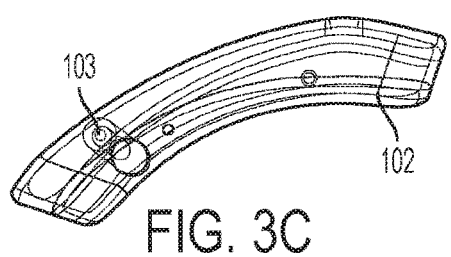
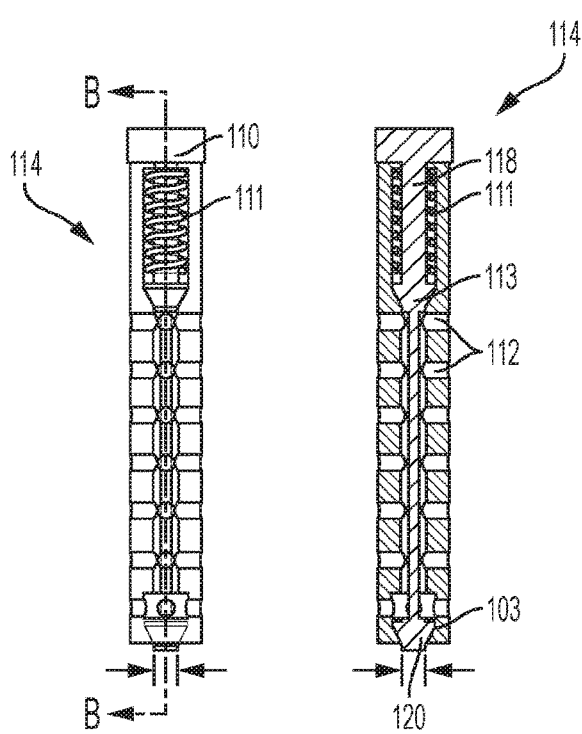

SURGICAL DRAIN SYSTEM AND METHOD OF USE

CROSS-REFERENCE TO RELATED APPLICATIONS

This application claims the benefit of and priority to U.S. Provisional Patent 62/105,343, filed Jan. 20, 2015, which is incorporated in its entirety in this document by reference.

BACKGROUND

The following disclosure relates to medical devices, systems, and methods, including, for example, a surgical drain system and method of use during and following surgery.

Surgical drains may be "open" or "closed" systems. An "open" system provides a conduit to maintain a pathway from within the body to outside the body. A "closed" drain is comprised of a drain portion and collection portion. A variety of closed surgical drain assemblies currently exist in which a portion may be left within the body of the patient during surgery and are connected to a collection portion of the system to accumulate the blood or fluid effluent.

Most commonly, existing systems consist of a single drain portion placed within the body of the patient, and a collection portion which accepts a single drain portion. Here, the collection portion contains a closable port which may be opened to allow the fluid within it to be evacuated and also to allow the air to be expelled from the collection portion such that a vacuum can be re-created by collapse of the collection portion. Subsequently, the closable port is closed whilst manually maintaining the collapse of the collection portion.

There are two primary types of collection portions: 1) a collapsible silicon or polymer collection portion that creates a weak vacuum by nature of its material composition and design, returning the collection portion to the un-collapsed state; and 2) a typically stronger vacuum collection portion which contains a spring or a plurality of springs that forcibly return the collecting portion to its un-collapsed state.

Limitations of current systems are several: 1) emptying the systems are cumbersome, 2) management of the collection portions is difficult for the patient, given that the collection portions may hang free, be pinned to clothing, or be held within some type of worn "pocket", 3) loose drain portions are frequently pulled out of the body inadvertently, which leads to uncontrolled drainage through the skin with the accompanied high risk of infection, and 4) re-creation of vacuum is cumbersome as the port is left open during the re-collapse of the collecting system process and must be closed whilst maintaining the collapsed state.

Accordingly, it remains desirable to address the limitations of conventional drainage systems, including but not limited to those limitations discussed above.

SUMMARY

Presented herein are systems, methods, and apparatus for surgical wound drainage and drain management. The drain collection system allows for collection of blood or fluid from one or multiple drain portions, can be worn on the patient's body, and embodies technology to better maintain the "closed" drainage that minimizes potential contamination of the interior of the drain system.

The method described herein simplifies the process of emptying and re-creating the vacuum within the collection portion.

Related methods of operation are also provided. Other apparatuses, methods, systems, features, and advantages of the location device will be or become apparent to one with skill in the art upon examination of the following figures and detailed description. It is intended that all such additional apparatuses, methods, systems, features, and advantages be included within this description, be within the scope of the location device, and be protected by the accompanying claims.

BRIEF DESCRIPTION OF THE DRAWINGS

The accompanying drawings, which are incorporated in and constitute a part of this specification, illustrate certain aspects of the instant invention and together with the description, serve to explain, without limitation, the principles of the invention.

FIG. 1A is a front view and FIG. 1B is a side view of a drain system worn on the body illustrating that the drain system is a low-profile system that may be worn beneath a user's clothing or worn while showering or dressing, according to one aspect.

FIG. 2 is a front view of one embodiment of a drain system in which a pump mechanism is used to generate a vacuum within a separate collection reservoir, and in which portions of a drain mechanism of the collection reservoir positioned in the interior of the collection reservoir are illustrated for clarity, according to one aspect.

FIG. 3A is a top view of the collection reservoir of FIG. 2, in which portions of the interior and bottom of the collection reservoir are illustrated for clarity.

FIG. 3B is a side view of the collection reservoir of FIG. 2, in which portions of a drain mechanism of the collection reservoir positioned in the interior of the collection reservoir are illustrated for clarity.

FIG. 3C is a bottom view of the collection reservoir of FIG. 2, in which portions of the interior and top of the collection reservoir are illustrated for clarity.

FIG. 4A is a side view of the drain mechanism, according to one aspect.

FIG. 4B is a cross-sectional view of the drain mechanism of FIG. 4A taken along line B-B, according to one aspect.

DETAILED DESCRIPTION

Figure 5:
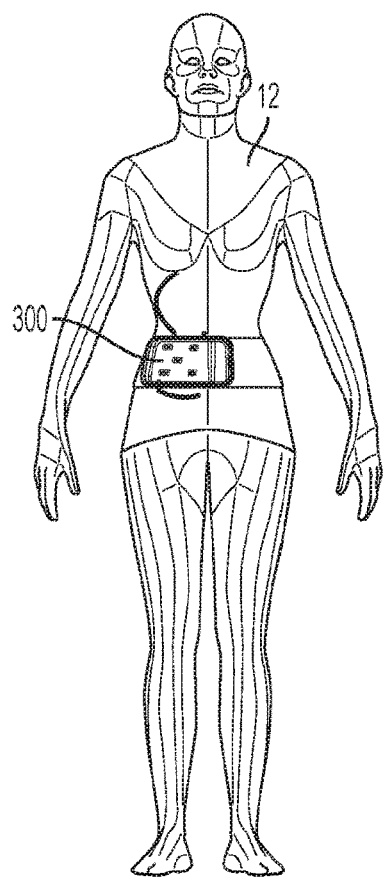
FIG. 5 is a front view showing a second embodiment of a drain system worn on the body illustrating that the drain system is a low-profile system that may be worn beneath a user's clothing or worn while showering or dressing, according to one aspect.

The present systems and apparatuses and methods are understood more readily by reference to the following detailed description, examples, drawing, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "a" component can include two or more such components unless the context indicates otherwise. Also, the words "proximal" and "distal" are used to describe items or portions of items that are situated closer to and away from, respectively, a user or operator such as a surgeon. Thus, for example, the tip or free end of a device may be referred to as the distal end, whereas the generally opposing end or handle may be referred to as the proximal end.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

The term "substantially" as used herein may be applied to modify any quantitative representation which could permissibly vary without resulting in a change in the basic function to which it is related.

A drain system 10 worn on the body of a user 12 is illustrated in FIGS. 1A and 1B, with a front view (FIG. 1A), and a side view (FIG. 1B). It can be readily appreciated that the drain system can be low in profile, and can be worn without clothing while dressing or showering, and can be worn beneath clothing. Optionally, because of the low profile, the drain system 10 can be worn beneath clothing without being detectable by other people.

Referring now to FIG. 2, the drain system 10 according to one embodiment is illustrated. In one aspect, the drain system comprises at least one of a collection tube 100, a collection reservoir 102, a belt 104 and a pump mechanism 106. In one aspect, at least a portion of the drain system, such as the collection tube, the collection reservoir and/or the pump mechanism can be attached to the belt so that the user can easily strap the system to his/her body.

In one aspect, a distal end of the collection tube 100 can be positioned within or adjacent to a portion of the user's body, and a proximal end of the collection tube can be coupled to a collection port 101 so that fluid (such as blood and the like) from the body can travel through an inner lumen of the collection tube 100 and into an interior chamber of the collection reservoir 102 through the collection port. In another aspect, the collection port 101 can comprise a first one-way valve to prevent reflux of fluid (that is, to prevent fluid from traveling from the collection reservoir, through the collection tube and into the body).

In a further aspect, the collection reservoir 102 can be charged with a vacuum force by the pump mechanism 106. That is, at least a portion of the pump mechanism can be in sealed fluid communication with the interior chamber of the collection reservoir so that vacuum pressure created by the pump mechanism 106 can be transmitted to the interior chamber. In one aspect, a pump connector 105 can be positioned between the pump mechanism 106 and the collection reservoir. For example, a distal end of the pump connector can be coupled to the pump mechanism and a proximal end of the pump connector 105 can be coupled to the collection reservoir at a pump port 108 defined in the reservoir wall. In use, at least a portion of the pressure and/or vacuum forces created by the pump mechanism 106 can be transmitted through an inner lumen of the pump connector and into the interior chamber of the collection reservoir 102.

In one aspect, the pump mechanism can further comprise at least one one-way valve. In this aspect, a second one-way valve can be positioned between the pump mechanism 106 and the collection reservoir 102 so that the pump mechanism can create a vacuum within the interior chamber of the collection reservoir rather than force pressure into the collection reservoir 102. That is, the second one-way valve can allow gas to be removed from the collection reservoir while preventing gas from undesirably entering the collection reservoir 102.

In another aspect, a third one-way valve 107 can be coupled to a portion of the pump mechanism 106 to allow air and/or other gases to escape from the pump mechanism into the atmosphere when the pump is activated. The pump mechanism 106 can be activated multiple times, if necessary, to generate a desired vacuum within the interior chamber of the collection reservoir 102. For example and without limitation, the pump mechanism can comprise a bellows-type pump that can be activated by depressing an outer portion of the pump mechanism 106. In another example, the pump can comprise a battery powered pump configured to create a desired vacuum force.

In use, the pump mechanism 106 can be activated, thereby creating a vacuum pressure in the interior chamber of the collection reservoir 102. The vacuum pressure can urge fluid from the body into the collection reservoir. The collected fluid can be released through a drain port 103 defined in a reservoir wall of the collection reservoir and into a drain tube 109 which can be directed to drain the collected fluid out of the system for disposal, or optionally into a container for measurement of the drain output.

FIGS. 3A-3C show further detail of the collection reservoir 102, according to one aspect. Again illustrated is the collection port 101 for coupling the collection reservoir to the collection tube 100 coming from the user, the pump port

108 for coupling of the collection reservoir to the pump mechanism 106, and the drain port 103 where fluid can leave the collection reservoir.

Referring now to FIGS. 3A-3C and 4, in one aspect, the collection reservoir 102 can comprise a drain mechanism 114 that can simultaneously allow air to enter and fluid to leave the interior chamber of the collection reservoir. In another aspect, the drain mechanism can comprise at least one of a knob 110 and a plunger 113. In this aspect, at least a portion of the knob can be positioned outside of the collection reservoir and can be configured to seal an air intake aperture 116 defined in a wall of the collection reservoir 102. That is, the air intake aperture of the collection reservoir can place the interior chamber of the collection reservoir 102 in fluid communication with the outside atmosphere, and a portion of the knob 110 can be sized and shaped to prevent or restrict the flow of air through the air intake aperture.

The knob 110 can be positioned on a distal end 118 of the plunger 113 and a proximal end 120 of the plunger can be sized and shaped to seal the drain port 103 defined in the collection reservoir. Thus, at least a portion of a central portion of the plunger can extend through the interior chamber of the collection reservoir. In one aspect, the plunger can be selectively moved about and between a first, sealed position and a second, unsealed position. In the first, sealed position, the air intake aperture 116 can be sealed by the knob 110 and the drain port 103 can be sealed by the proximal end of the plunger 113. In the second, open position, the knob 110 can be spaced from the air intake aperture a first predetermined distance and the proximal end 120 of the plunger can be spaced from the drain port 103 a second predetermined distance. Because the knob 110 and the proximal end 120 of the plunger 113 are linearly aligned and can move the same amount, the first distance can be equal to the second distance. As can be appreciated, in the second, open position, the air intake aperture is not sealed by the knob 110 on the distal end 118 of the plunger 113, and the drain port 103 is not sealed by the proximal end 120 of the plunger. Thus, in the second, open position, air from the atmosphere can enter the interior chamber of the collection reservoir through the air intake aperture 116, and simultaneously, fluid from the collection reservoir 102 can drain through the drain port 103. In one aspect, at least one spring 111 or other biasing element can be positioned to urge the plunger to the first, closed position. That is, the spring can keep the plunger 113 in the closed position, unless a user exerts a force on the knob to move the plunger to the second open position.

In one aspect, a plurality of channels 112 can be defined in a portion of the drain mechanism 114. In this aspect, the plurality of channels 112 can provide a path for fluid to enter the plunger from the interior chamber of the collection reservoir 102 and to exit the drain port 103 at the bottom of the collection reservoir.

In use, the pump mechanism 106 can be activated to create a desired vacuum force in the interior chamber of the collection reservoir 102. Fluid from the body of the user 12 can enter the interior chamber of the collection reservoir through the collection tube 100 and the collection port 101. The spring 111 can position the plunger 113 in the first, closed position so that fluid does not inadvertently drain through the drain port 103. Upon desiring to drain fluid form the collection reservoir, the user can pull the knob 110 so that the plunger is moved to the second, open position. In the second, open position, the drain port is not blocked so fluid from the interior chamber can drain through the drain port 103, and air can enter the interior chamber through the air intake aperture 116. Thus, emptying the system can be easily accomplished. Further, the force exerted by the spring 111 on the plunger can be selected so that inadvertent movement of the plunger to the open position can be prevented. Re-creation of the vacuum in the interior chamber can also be easily accomplished by further activation of the pump mechanism with the plunger 113 in the first, closed position.

In use then, the drain collection system 10 allows for collection of blood or other fluid from at least one drain portion of the body of the user into the collection reservoir 102. The drain system can be worn discreetly beneath the clothing of the user 12. Further, in one aspect, the drain mechanism 114 better maintains the drain system 10 as a "closed" system that minimizes potential contamination of the interior of the drain system when compared to conventional drainage systems.

With reference now to FIG. 5, a front view of a user 12 wearing a second embodiment of a drain system 300 is illustrated. In one aspect, the drain system can comprise a collection reservoir 303 which can be charged with a vacuum pressure without using a separate pump.

Figure 6:
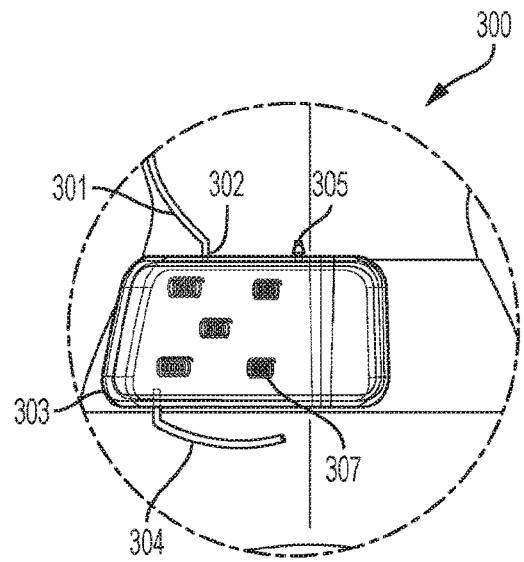
FIG. 6 is a front view of the second embodiment of a drain system, in which portions of a drain mechanism of the collection reservoir positioned in the interior of the collection reservoir are illustrated for clarity, according to one aspect.

FIG. 6 illustrates the second embodiment of the drain system 300. In this embodiment, according to one aspect, a portion of the collection reservoir 303 itself can be collapsed to generate a vacuum force. That is, a portion of the collection reservoir can act as a pump, such as for example and without limitation, a bellows pump to create a desired vacuum force.

In use, a collection tube 301 coming from the user 12 can couple to the collection reservoir 303 at a collection port 302 defined in the collection reservoir, which can have a one-way valve to prevent reflux of fluid into the collection tube 301. An air port 305 for air to escape from the collection reservoir can be defined in a wall of the collection reservoir 303. The collection reservoir can comprise an air one-way valve to allow air or other fluid to leave the interior chamber, while preventing air from undesirably entering into the interior chamber through the air port 305. The collection reservoir 303 can be drained to allow the fluid in the interior chamber to leave the collection reservoir by opening a port to let air into the reservoir (at air port 305 or another point not shown) and opening a valve at a drain port 306 to allow fluid into a drain tube 304. The collection reservoir 303 can then be recharged by depressing the face of the reservoir to force air out of the air one way valve at the air port 305, thereby creating the desired vacuum pressure.

Figure 7A:
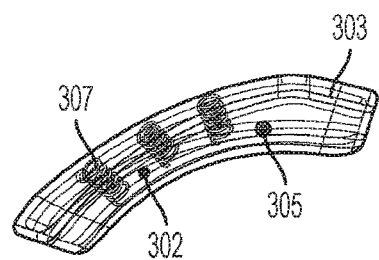
FIG. 7A is a top view of the collection reservoir of FIG. 6, in which portions of the interior and bottom of the collection reservoir are illustrated for clarity.
Figure 7B:
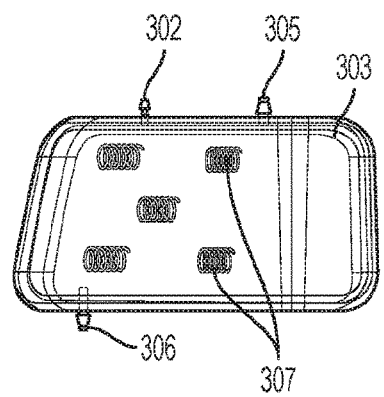
FIG. 7B is a side view of the collection reservoir of FIG. 6, in which portions of a biasing element of the collection reservoir positioned in the interior of the collection reservoir are illustrated for clarity.
Figure 7C:
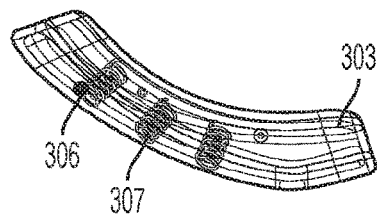
FIG. 7C is a bottom view of the collection reservoir of FIG. 2, in which portions of the interior and top of the collection reservoir are illustrated for clarity.

FIGS. 7A-7C show greater detail of the collection reservoir 303 of the second embodiment, according to one aspect. As can be seen, at least one spring 307 or other biasing element can be positioned in the interior chamber of the collection reservoir 303. The at least one spring can be compressed by the user 12 when the user depresses the face of the collection reservoir to create the desired vacuum in the interior chamber. In another aspect, at least a portion of the collection reservoir 303, such as a face, can have a solid component that would be pressed upon by the user. Optionally, at least a portion of the collection reservoir, such as the sides and/or the wall around the collection reservoir 303 circumferentially can be flexible and compressible.

It should be noted that a drain mechanism such as drain mechanism 114 illustrated in FIGS. 4A-4B could also be used in this second embodiment to allow for effluent to be drained from the collection reservoir 303 in a single step of pulling up on the knob 110.

In use, the drain collection system 300 allows for collection of blood or other fluid from at least one drain portion of the body of the user 12 into the collection reservoir 303. The drain system can be worn discreetly beneath the clothing of the user 12. Further, in one aspect, the drain system 10 is a "closed" system that minimizes potential contamination of the interior of the drain system when compared to conventional drainage systems.

Although several aspects of the invention have been disclosed in the foregoing specification, it is understood by those skilled in the art that many modifications and other aspects of the invention will come to mind to which the invention pertains, having the benefit of the teaching presented in the foregoing description and associated drawings. It is thus understood that the invention is not limited to the specific aspects disclosed hereinabove, and that many modifications and other aspects are intended to be included within the scope of the appended claims. Moreover, although specific terms are employed herein, as well as in the claims that follow, they are used only in a generic and descriptive sense, and not for the purposes of limiting the described invention.

What is claimed is:

1. A wearable surgical drain system for collection of fluid from a body of a user, the drain system comprising:
   a collection reservoir having a reservoir wall that defines an interior chamber and a collection port defined in a portion of the reservoir wall, wherein a drain port is defined in a portion of the reservoir wall, and wherein the drain port is configured to allow fluid collected in the interior chamber of the collection reservoir to be released;
   a collection tube having a distal end configured to be coupled to or in fluid communication to the user and a proximal end coupled to the collection port such that the distal end and an inner lumen of the collection tube, the collection port and the interior chamber of the collection reservoir; are in sealed fluid communication,
   a pump mechanism configured to charge the interior chamber of the collection reservoir with a vacuum pressure such that, when charged, the vacuum pressure urges fluid from the user through the inner lumen of the connection tube, through the collection port and into the interior chamber of the collection reservoir wherein, an air intake aperture is defined in a portion of the reservoir wall of the collection reservoir, and wherein the air intake aperture is configured to place the interior chamber of the collection reservoir in fluid communication with the outside atmosphere, wherein the collection port comprises a first one-way valve configured to prevent fluid from traveling out of the interior chamber of the collection reservoir through the collection port and a second one-way valve configured to allow gas to be removed from the interior chamber of the collection reservoir while preventing gas from undesirably entering the interior chamber of the collection reservoir;
   wherein the collection reservoir comprises a drain mechanism configured to simultaneously allow air to enter and fluid to exit the interior chamber of the collection reservoir, wherein the drain mechanism comprises a knob and a plunger, wherein the plunger has a distal end on which the knob is positioned, a proximal end of the plunger is configured to seal the drain port and a central portion extending between the proximal end and the distal end of the plunger wherein a plurality of channels are defined in a portion of the drain mechanism plunger which extends fully along a length of the central portion to the distal end of the drain mechanism plunger, and wherein the plurality of channels provide a path for fluid to enter the plunger from the interior chamber of the collection reservoir and to exit the drain port; and a belt configured to be worn by the user, wherein the wearable surgical drain system including the collection reservoir, the collection tube, the pump mechanism and drain mechanism are attachable to the belt so that the wearable surgical drain system is configured to be wearable by the user without clothing while dressing or showering and worn under clothing without being detectable.

2. The drain system of claim 1, wherein a pump port is defined in a portion of the reservoir wall of the collection reservoir.

3. The drain system of claim 2, further comprising a pump connector having a distal end coupled to the pump mechanism and a proximal end coupled to the pump port of the collection reservoir such that at least a portion of the vacuum pressure created by the pump mechanism is transmitted through an inner lumen of the pump connector and into the interior chamber of the collection reservoir.

4. The drain system of claim 1, further comprising a drain tube coupled to the drain port, wherein the drain tube is configured to direct fluid exiting the interior chamber of the collection reservoir through the drain port out of the drain system.

5. The drain system of claim 1, wherein at least a portion of the knob is positioned outside of the interior chamber of the collection reservoir and is configured to selectively seal the air intake.

6. The drain system of claim 5, wherein at least a portion of the central portion of the plunger extends through the interior chamber of the collection reservoir.

7. The drain system of claim 6, wherein the plunger is selectively movable about and between a first, sealed position, in which the air intake aperture is sealed by the knob and the drain port is sealed by the proximal end of the plunger and a second, open position, in which, the knob is spaced from the air intake aperture a first predetermined distance and the proximal end of the plunger is spaced from the drain port a second predetermined distance that equals the first predetermined distance.

8. The drain system of claim 6, wherein the plunger is selectively movable about and between a first, sealed position, in which the air intake aperture is sealed by the knob and the drain port is sealed by the proximal end of the plunger and a second, open position, in which, the air intake aperture is not sealed by the knob and the drain port is not sealed by the proximal end of the plunger.

9. The drain system of claim 8, wherein the drain mechanism further comprises a biasing element configured to urge the plunger to the first, sealed position.

\* \* \* \* \*